United States Patent [19]

Caruso et al.

[11] Patent Number: 5,567,829
[45] Date of Patent: Oct. 22, 1996

[54] METHOD FOR RECOVERING PHENOL AND XANTHENE VALUES FROM WASTE POLYCARBONATE

[75] Inventors: Andrew J. Caruso; Julia L. Lee, both of Schenectady, N.Y.

[73] Assignee: General Electric Company, Schenectady, N.Y.

[21] Appl. No.: 422,472

[22] Filed: Apr. 17, 1995

[51] Int. Cl.$^6$ .......................... C07D 311/82; C07C 69/96; C07C 37/68
[52] U.S. Cl. .......................... 549/388; 558/274; 568/749
[58] Field of Search .......................... 549/388; 558/274; 568/749

[56] References Cited

U.S. PATENT DOCUMENTS

| 5,336,814 | 8/1994 | Shafer | 568/753 |
| 5,430,199 | 7/1995 | Caruso et al. | 568/724 |

*Primary Examiner*—Nicky Chan
*Attorney, Agent, or Firm*—William H. Pittman

[57] ABSTRACT

Organic values are salvaged from scrap polycarbonate by heating in the presence of an acid catalyst and a $C_{1-4}$ alkyl phenol such as m- or p-cresol. Among the compounds which can be salvaged are polyalkylated xanthenes, phenol and diaryl carbonate.

17 Claims, No Drawings

METHOD FOR RECOVERING PHENOL AND XANTHENE VALUES FROM WASTE POLYCARBONATE

BACKGROUND OF THE INVENTION

The present invention relates to a method for recycling waste polycarbonate to produce a variety of useful products.

As shown in commonly owned application Ser. No. 08/218,397, now U.S. Pat. No. 5,430,149, phenol and xanthene values, such as 3,6,9,9-tetramethylxanthene, can be obtained by treating bisphenol tar in the presence of an acid catalyst and alkylated phenol at an elevated temperature. The 3,6,9,9-tetramethylxanthene can be used as a heat transfer fluid or converted to a polyester intermediate such as a xanthenedicarboxylic acid. U.S. Pat. No. 5,336,814 is directed to a method for treating polycarbonate scrap by basic phenoylsis to salvage a variety of organic values such as bisphenol A, diphenyl carbonate and phenol.

It would be desirable to provide additional methods for salvaging organic values from waste polycarbonate to obtain a variety of organic polymeric intermediates.

SUMMARY OF THE INVENTION

The present invention is based on the discovery that heating scrap aromatic polycarbonate in the presence of an alkylated phenol and an acid catalyst can result in essentially complete depolymerization. Surprisingly, the bisphenol structural unit derived from the polycarbonate backbone is fragmented into 2 equivalents of phenol. The residual ispropylidene group present in the bisphenol structural unit is intercepted by the alkylated phenol to produce polyalkylated xanthenes. Diaryl carbonates may also be products.

The invention is a method for salvaging organic values from scrap aromatic polycarbonate comprising effecting reaction, at a temperature of 100°–250° C. and in the presence of an effective amount of a strong acid catalyst, a mixture comprising scrap aromatic polycarbonate and a $C_{1-4}$ alkylated phenol, the weight ratio of said alkylated phenol to said scrap polycarbonate being about 2–1000:1.

DETAILED DESCRIPTION; PREFERRED EMBODIMENTS

Scrap polycarbonate articles which can be converted in accordance with the present invention to valuable organic values include crushed milk jugs and eyeglass frames. Polycarbonates which can be salvaged are preferably bisphenol A polycarbonates. However, polycarbonates made from other bisphenols, such as aromatic o- and p-bisphenols and tetramethylbisphenol, also can be treated.

The polyalkylated xanthenes which are obtainable by the method of the invention include those of the formula

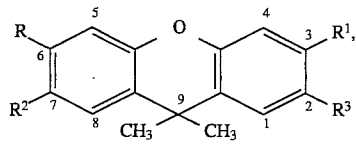

where each of R, $R^1$, $R^2$ and $R^3$ is independently hydrogen or a $C_{1-4}$ alkyl radical, at least two of R–$R^3$ being alkyl. Examples are 3,6,9,9-tetramethylxanthene, 2,7,9,9-tetramethylxanthene, 2,6,9,9-tetramethylxanthene and 2,3,6,7,9,9-hexamethylxanthene. Such polyalkylated xanthenes can be used as heat transfer fluids. As shown in copending, commonly owned application Ser. No. 08/218,397, they also can be converted to polyester intermediates such as xanthenedicarboxylic acids and their halides and esters.

The preferred $C_{1-4}$ alkyl phenols which are used as reactants in the method of the present invention are m- and p-cresol. Some of the dialkyl phenols which can be used are 3,4-dimethylphenol, 3-ethyl-4-methylphenol, 4-ethyl-3-methylphenol, 4 -butyl-3-methylphenol and 3-butyl-4-methylphenol.

Suitable strong acid catalysts are acids having a pKa in the range from about −12 to about 1. There are included methanesulfonic acid, p-toluenesulfonic acid, camphorsulfonic acid and various aromatic resin-bound sulfonic acids as exemplified by Nation® ion exchange beads. An effective amount of acid catalyst is about 0.1–50% by weight based on the total weight of the reaction mixture. The reaction can be conducted or at pressures in the range of about 1–75 atmospheres, under sealed conditions if desired.

Experience has shown that distillation of the phenolic materials from the polyalkylated xanthene reaction mixture can be effected at a temperature in the range of about 70°–240° and preferably 70°–90° C. Among the phenolic materials which may be recovered in this way is the alkylated phenol employed as a reagent. Separate recovery of a monohydroxyaromatic compound corresponding in molecular structure to the polycarbonate units as illustrated by phenol in the case of a bisphenol A polycarbonate, free from more highly alkylated phenol such as a cresol, can be achieved in a subsequent distillation step as shown in U.S. Pat. No. 4,325,789 which is incorporated herein by reference. A component such as chlorotoluene can be employed to form an azeotrope with the phenol and effect separation from the cresol. Final recovery of the phenol can be achieved by a second distillation in the presence of water.

The polyalkylated xanthenes can be obtained by distillation which can be effected at a temperature in the range of about 120°–280° C. and a pressure in the range of about 0.01–1.0 torr. Alternatively, the polyalkylated xanthenes can be separated from the reaction mixture by a standard recrystallization procedure.

The invention is illustrated by the following examples.

EXAMPLE 1

A mixture of 101 mg of polycarbonate (0.398 equivalent of bisphenol A), 2 mL of m-cresol, 2 mL of p-cresol and 40 mg of methanesulfonic acid was heated under sealed conditions for 35 hours at 150° C. Gas chromatographic (GC) analysis showed that a quantitative yield of phenol was obtained. In addition, there was obtained a mixture of 17 mg (18% yield) of 3,6,9,9-tetramethylxanthene, 23 mg (25% yield) of 2,7,9,9-tetramethylxanthene and 44 mg(45% yield) of 2,6,9,9-tetramethylxanthene. The identities of the various xanthenes were further confirmed by gas chromatographic mass spectrographic analysis (GCMS). Significant amounts of dicresyl carbonates were also observed.

Standard recovery techniques such as distillation and recrystallization could be used to recover the respective ingredients. The xanthenes could be oxidized to the corresponding dicarboxylic acids if desired to provide intermediates for making high performance xanthene polyesters.

EXAMPLE 2

A mixture of 103.3 mg of polycarbonate (0.41 equivalent of bisphenol A), 4 mL of p-cresol and 40 mg of methanesulfonic acid was heated under sealed conditions for 35 hours at 150° C. Gas chromatographic analysis showed that there was obtained a quantitative yield of phenol; a 79% yield of 2,7,9,9-tetramethylxanthene (77 mg) was also obtained. Peak assignments were confirmed by GCMS. The presence of substantial quantities of di-p-cresyl carbonate was also established.

EXAMPLE 3

A mixture of 100 mg (0.394 equivalent of bisphenol A) of polycarbonate, 2.0 mL of m-cresol and 19 mg of methanesulfonic acid was heated at 150° C. for 72.5 hours. The reaction mixture was cooled and diluted in the presence of 105.8 mg of tetradecane as an internal standard. It was assayed by GC; the analysis showed 65 mg (88% yield) of phenol and 81 mg (86% yield) of 3,6,9,9-tetramethylxanthenene.

What is claimed is:

1. A method for salvaging organic values from scrap aromatic polycarbonate comprising effecting reaction, at a temperature of 100°–250° C. and in the presence of an effective amount of a strong acid catalyst, a mixture comprising scrap aromatic polycarbonate and a $C_{1-4}$ alkylated phenol, the weight ratio of said alkylated phenol to said scrap polycarbonate being about 2–1000:1.

2. A method in accordance with claim 1 where the scrap polycarbonate is bisphenol A polycarbonate.

3. A method in accordance with claim 1 where the alkylated phenol is m-cresol.

4. A method in accordance with claim 1 where the alkylated phenol is p-cresol.

5. A method in accordance with claim 1 where the alkylated phenol is a mixture of m-cresol and p-cresol.

6. A method in accordance with claim 1 where the alkylated phenol is a 3,4 di-($C_{1-4}$ alkyl) phenol.

7. A method in accordance with claim 1 wherein the catalyst is methanesulfonic acid.

8. A method in accordance with claim 1 wherein a polyalkylated xanthene is recovered from said mixture.

9. A method in accordance with claim 8 where the polyalkylated xanthene is 3,6,9,9-tetramethylxanthene.

10. A method in accordance with claim 8 where the polyalkylated xanthene is 2,7,9,9-tetramethylxanthene.

11. A method in accordance with claim 1 where the polyalkyated xanthene is 2,6,9,9-tetramethylxanthene.

12. A method in accordance with claim 1 wherein a diaryl carbonate is recovered from said mixture.

13. A method in accordance with claim 12 where the diaryl carbonate is at least one of di-m-cresyl carbonate and di-p-cresyl carbonate.

14. A method in accordance with claim 1 where the alkylated phenol employed as a reagent is recovered from said mixture.

15. A method in accordance with claim 14 where said alkylated phenol is m-cresol or p-cresol.

16. A method in accordance with claim 1 where a monohydroxyaromatic compound corresponding in molecular structure to the units in said polycarbonate is recovered.

17. A method in accordance with claim 16 where said hydroxyaromatic compound is phenol.

* * * * *